United States Patent [19]
Matukuma et al.

[11] Patent Number: 4,612,327
[45] Date of Patent: Sep. 16, 1986

[54] REPELLENT COMPOSITIONS AGAINST INSECTS, TICKS AND MITES EMPLOYING MIXTURES OF O-ALKYL-N-PHENYLTHIOCARBAMATES AND DEET

[75] Inventors: Akira Matukuma, Kanagawa; Yohji Takahashi, Tokyo; Yoshihiko Kondo, Chiba, all of Japan

[73] Assignee: Mitsubishi Chemical Industries, Ltd., Tokyo, Japan

[21] Appl. No.: 722,257

[22] Filed: Apr. 12, 1985

[30] Foreign Application Priority Data

Apr. 13, 1984 [JP] Japan .................................. 59-74738

[51] Int. Cl.⁴ ............................................. A01N 47/10
[52] U.S. Cl. ........................... 514/479; 424/DIG. 10; 514/919
[58] Field of Search ............... 424/DIG. 10; 514/478, 514/479, 617, 919

[56] References Cited

FOREIGN PATENT DOCUMENTS 1139694 11/1960 Fed. Rep. of Germany .
56-73008 6/1981 Japan .................................. 514/919

Primary Examiner—Allen J. Robinson
Attorney, Agent, or Firm—Sughrue, Mion, Zinn, Macpeak & Seas

[57] ABSTRACT

A repellent composition against insects, ticks and mites, comprising the two components, an O-alkyl-N-phenylthiocarbamate and N,N-diethyl-m-toluamide.

4 Claims, No Drawings

REPELLENT COMPOSITIONS AGAINST INSECTS, TICKS AND MITES EMPLOYING MIXTURES OF O-ALKYL-N-PHENYLTHIOCARBAMATES AND DEET

FIELD OF THE INVENTION

The present invention relates to a repellent composition against insects, ticks and mites.

BACKGROUND OF THE INVENTION

Many insecticides have bee developed and used for the purposes of preventing and keeping off various insanitary or unpleasant, harmful insects. When application of insecticides is difficult or undesirable, however, repellents are used. Although many repellents are also known already, there are some problems about their effects and other respects and only a few of them are used practically. For instance, N,N-diethyl-m-toluamide (hereinafter abbreviated as Deet) described in U.S. Pat. No. 2,932,665 is already used practically as a repellent. However, its effect disappears within a relatively short period of time and the effect also is not always satisfactory. On the other hand, O-alkyl-N-phenylthiocarbamates are disclosed in German Pat. No. 1,139,694 to have a miticidal effect, but no description is given therein as regards their repellent effect. According to the knowledge of the present inventors, however, these O-alkyl-N-phenylthiocarbamates disclosed in the above-mentioned German patent have an unexpected property of showing an excellent repellent effect against insects, ticks and mites, although their insecticidal and miticidal effect is too weak to use them practically as an insecticide or miticide.

Thus, the present inventors have made various investigations for further improving the repellent effect of the O-alkyl-N-phenylthiocarbamates, particularly with the purposes of developing a repellent having an immediate and durable effect, and found that O-alkyl-N-phenylthiocarbamates having an alkyl group of the small number of carbon atoms have a relatively strong repellent effect and further that, by mixing such thiocarbamates with Deet, a superior effect to that which may be produced by adding the effects of the individual components can be obtained.

SUMMARY OF THE INVENTION

An object of the present invention is to provide a repellent composition against insects, ticks and mites, comprising at least one O-alkyl-N-phenylthiocarbamate of the formula (1):

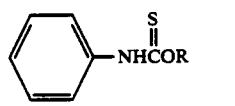

(1)

wherein R denotes an alkyl group of from 1 to 3 carbon atoms, and N,N-diethyl-m-toluamide as active ingredients.

The composition of the present invention exhibits an immediate and durable repellent effect which results from synergism of the two components contained therein. Further merits are that they are not irritative to the skin and are substantially odorless.

DETAILED DESCRIPTION OF THE INVENTION

As the O-alkyl-N-phenylthiocarbamate which is one component of the composition of the present invention, there can be exemplified those compounds of the formula (1) in which R is a methyl, ethyl, n-propyl, or i-propyl group. Above all, the compound having an ethyl group as R is preferable.

The ratio of mixing the compound of the formula (1) to Deet is from 0.05 to 3, preferably from 0.1 to 2.5, parts by weight, per part by weight of Deet.

There is no special limitation in the method of mixing the two components. They may be mixed with each other, for example, by dissolving them in a common solvent, such as ethyl alcohol, or by dissolving the compound of the formula (1) in Deet because Deet per se is a good solvent for the former. To dissolve the compound of the formula (1) in Deet without using any other solvent is especially preferable when a composition containing the active ingredients at a high concentration is desired.

The composition of the present invention may be used as such or in the form of emulsions, suspensions, dusts, tablets, creams, sprays and the like using suitable adjuvants. In these forms, the active ingredients, the two components of the present invention is contained usually in an amount of from 0.5 to 80, preferably from 2 to 40, percent by weight. Further, it is also possible to add other active ingredients, so far as they do not injure the synergism of the two components of the present invention.

Preparations in the form of emulsions or suspensions are prepared by adding suitable emulsifiers or dispersing agents to the composition of this invention which is dissolved beforehand in a suitable solvent. They are diluted with water or other solvents at the time of use. Dusts are prepared by mixing the composition of this invention with a solid carrier such as talc and pulverizing the mixture. Creams are prepared usually by using vaseline, glycerol, lanolin, zinc oxide, etc., as a substrate.

The repellent according to the present invention may be used by applying it to the skin or by impregnating clothes with it. It may be used also by painting or spraying it directly on the area where insects, ticks or mites should be repelled, or by painting or impregnating a sheet of paper, nonwoven fabric, plastic, etc., with it and spreading the sheet in drawers or closets or on the place inhabitable for cockroach and the like, such as the bottom of furniture.

The composition of the present invention is effective against various harmful or unpleasant insects, ticks and mites. For example, they repel mosquitos, cockroaches, ants, flies, tobacco beetles (*Lasioderma serricorme*), fluor beetles, moth, ticks, mites and the like.

As is evident from the following Examples, the composition of the present invention exhibits, by mixing the two components, a repellent effect which is not only immediate and durable but also far superior to that attained by using the components individually.

Hereinafter, the invention is explained in further detail by reference to the Examples. However, it is not to be construed that the invention is restricted thereto.

EXAMPLE 1

By mixing O-ethyl-N-phenylthiocarbamate (abbreviated as OEN) with N,N-diethyl-m-toluamide (Deet), samples having the following compositions were prepared:

Sample

A: ethanol solution containing 2.5% of OEN and 2.5% of Deet,
B: ethanol solution containing 5% of OEN and 5% of Deet,
C: ethanol solution containing 5% of Deet,
D: ethanol solution containing 5% of OEN.

Repelling Test against Mosquito (1)

Each of the above samples A to D was applied uniformly to the palm of the hand of human beings (dosage: 60 cc/m$^2$), and the palm was inserted into a cage in which 50 *Aedes albopictus* (female adults of 5 days after emergence, not yet sucked blood) were set free. Then, the number of mosquitos which came flying to the palm, stopped there for 2 seconds or longer and showed bloodsucking action, was determined by visual observation. When a non-treated palm of the hand of human being was inserted in the cage, 10 or more mosquitos showed the bloodsucking action within several seconds. At each lapse of time as prescribed, the palm was inserted into the cage for 5 minutes.

The results obtained are shown in Table 1. The numerical values given in the Table are the total values of the tests repeated twice.

TABLE 1

| Sample No. | Number of Mosquitos which Showed the Bloodsucking Action Lapse of Time (hours) | | | | | | | |
|---|---|---|---|---|---|---|---|---|
| | 1 | 2 | 3 | 4 | 5 | 6 | 7 | 8 |
| A | 1 | 0 | 0 | 2 | 0 | 1 | 0 | 1 |
| B | 0 | 0 | 0 | 0 | 1 | 0 | 0 | 0 |
| C | 0 | 0 | 0 | 0 | 0 | 5 | 4 | 4 |
| D | 1 | 2 | 0 | 0 | 1 | 1 | 1 | 3 |

Repelling Test against Mosquito (2)

Each of the samples A to D was applied uniformly to an individual bag made of wire gauge (dosage: 83 cc/m$^2$), and a mouse (mouse for bloodsucking) was driven into the bag. The bag was inserted into a cage in which 50 *Aedes albopictus* (female adults 5 days after emergence, not yet sucked blood) were set free, and allowed to stand overnight. In the next morning, all mosquitos were crushed on a filter paper, and the number of mosquitos which had sucked blood was calculated.

The results obtained are shown in Table 2.

TABLE 2

| Sample No. | Number of Mosquitos which Sucked Blood |
|---|---|
| A | 0 |
| B | 0 |
| C | 2 |
| D | 2 |
| Non-Treated | 38 |

EXAMPLE 2

Repelling Test against German Cockroach (*Blattella germanica*)

20 adults (10 females and 10 males) of the german cockroach were released into a plastic container (35(W)×26(D)×6(H)cm) with water. The cockroaches were offered a choice of two shelters (8(W)×6.5(D)×1(H)cm), one of which was treated with a repellent. The shelter was treated immediately before the test by pipetting 1 ml acetone solution of chemical on the entire inner surface. When the acetone had completely evaporated, a treated and non-treated shelters were placed in a container with cockroaches. The cockroaches were counted on 2 days after setting. After counting, the insects were shaken out of their shelters and the two shelters reversed to force the insects to make another choice. And 10 days after setting, the cockroaches were counted again. The experiment was replicated two times.

The results obtained are shown in Table 3.

TABLE 3

| Chemical | Ratio (W/W) | Dosage (g-a.i./m$^2$) | Repl. | Number of Cockroaches | | | | | |
|---|---|---|---|---|---|---|---|---|---|
| | | | | 2 Days after Setting | | | 10 Days after Setting | | |
| | | | | Treated Shelter | Non-Treated Shelter | Outside Shelter | Treated Shelter | Non-Treated Shelter | Outside Shelter |
| Deet | | 1 | 1 | 0 | 20 | 0 | 8 | 12 | 0 |
| | | | 2 | 0 | 18 | 2 | 7 | 13 | 0 |
| | | 0.5 | 1 | 17 | 1 | 2 | 10 | 9 | 1 |
| | | | 2 | 8 | 12 | 0 | 15 | 5 | 0 |
| | | 0.25 | 1 | 11 | 8 | 2 | 12 | 8 | 0 |
| | | | 2 | 9 | 11 | 1 | 8 | 12 | 0 |
| OEN | | 1 | 1 | 0 | 20 | 0 | 1 | 18 | 1 |
| | | | 2 | 0 | 20 | 0 | 0 | 18 | 2 |
| | | 0.5 | 1 | 1 | 18 | 1 | 2 | 18 | 0 |
| | | | 2 | 2 | 18 | 0 | 1 | 19 | 0 |
| | | 0.25 | 1 | 6 | 14 | 0 | 7 | 12 | 1 |
| | | | 2 | 3 | 15 | 2 | 3 | 16 | 1 |
| Deet + OEN | 1:1 | 1 | 1 | 0 | 19 | 1 | 0 | 18 | 2 |
| | | | 2 | 0 | 18 | 2 | 2 | 16 | 2 |
| | | 0.5 | 1 | 0 | 20 | 0 | 0 | 20 | 0 |
| | | | 2 | 0 | 19 | 1 | 0 | 19 | 1 |
| | | 0.25 | 1 | 0 | 19 | 1 | 1 | 19 | 0 |
| | | | 2 | 0 | 19 | 1 | 0 | 19 | 1 |
| Deet + OEN | 4:1 | 1 | 1 | 0 | 20 | 0 | 0 | 19 | 1 |
| | | | 2 | 0 | 20 | 0 | 0 | 20 | 0 |
| | | 0.5 | 1 | 0 | 20 | 0 | 1 | 19 | 0 |
| | | | 2 | 0 | 19 | 1 | 0 | 19 | 1 |
| | | 0.25 | 1 | 0 | 18 | 2 | 0 | 20 | 0 |
| | | | 2 | 0 | 19 | 1 | ·2 | 16 | 2 |

EXAMPLE 3

Repelling Test against Mold Mite (*Tynophagus putrescentiae*)

Around 4 g medium saturated with mold mites was put into a laboratory dish ($\phi$9.5 cm). And a corrugated cardboard (6×6 cm) was placed on the medium. 0.5 ml acetone solution of chemical was treated on a paper (5×5 cm). After the acetone evaporated, the paper was set on the cardboard. A non-treated paper (3×3 cm) was put on the treated paper. After one night, the number of mold mites on the non-treated paper was counted. The experiment was replicated four times.

The results obtained are shown in Table 4.

TABLE 4

| Chemical | Ratio (W/W) | Dosage (g-a.i./m$^2$) | Number of Mold Mites on Non-Treated Paper* |
| --- | --- | --- | --- |
| Deet |  | 1 | 87.5 |
|  |  | 0.25 | >200 |
|  |  | 0.0625 | >200 |
| OEN |  | 1 | 3.25 |
|  |  | 0.25 | 9.0 |
|  |  | 0.0625 | 35.5 |
| Deet + OEN | 1:1 | 1 | 0 |
|  |  | 0.25 | 0 |
|  |  | 0.0625 | 3.0 |
| Deet + OEN | 4:1 | 1 | 0 |
|  |  | 0.25 | 1.25 |
|  |  | 0.0625 | 7.5 |

*Average number in 4 replications.

EXAMPLE 4

Repelling Test against Ant (*Monomorium spp.*)

A filter paper (3×13 cm) was treated by 2 ml acetone solution of chemical. After drying, the filter paper was fixed on a glass plate (20×15 cm) with a non-treated filter paper. A plastic cup ($\phi$13 cm) was placed upside down on the center of the two filter papers. The bottom of the cup was taken off. The inner surface of the cup was treated with liquid paraffin to inhibit ants from climbing. 10 ants were released in the cup. Numbers of ants on the treated filter paper were counted after 10, 60 and 600 minutes. The experiment was replicated four times.

The results obtained are shown in Table 5.

TABLE 5

| Chemical | Ratio (W/W) | Dosage (g-a.i./m$^2$) | Number of Ants on the Treated Filter Paper* | | |
| --- | --- | --- | --- | --- | --- |
|  |  |  | 10 Min. | 60 Min. | 600 Min. |
| Deet |  | 1 | 4 | 5 | 9 |
|  |  | 0.5 | 8 | 12 | 21 |
|  |  | 0.25 | 14 | 25 | 28 |
| OEN |  | 1 | 0 | 1 | 0 |
|  |  | 0.5 | 1 | 0 | 11 |
|  |  | 0.25 | 8 | 10 | 8 |
| Deet + OEN | 1:1 | 1 | 0 | 0 | 0 |
|  |  | 0.5 | 0 | 0 | 0 |
|  |  | 0.25 | 3 | 1 | 0 |
| Deet + OEN | 4:1 | 1 | 0 | 0 | 0 |
|  |  | 0.5 | 0 | 0 | 0 |
|  |  | 0.25 | 0 | 0 | 1 |

*Total number in 4 replications.

While the invention has been described in detail and with reference to specific embodiments thereof, it will be apparent to one skilled in the art that various changes and modifications can be made therein without departing from the spirit and scope thereof.

What is claimed is:

1. A repellent composition against insects, ticks and mites, comprising at least one O-alkyl-N-phenylthiocarbamate of the formula (1):

wherein R denotes an alkyl group of from 1 to 3 carbon atoms, and N,N-diethyl-m-toluamide, and wherein the weight ratio of the O-alkyl-N-phenylthiocarbamate of the formula (1) to N,N-diethyl-m-toluamide is from 0.05:1 to 3.0:1.

2. A composition of claim 1, wherein the weight ratio of the O-alkyl-N-phenylthiocarbamate of the formula (1) to N,N-diethyl-m-toluamide is from 0.1:1 to 2.5:1.

3. A composition of claim 1, wherein the O-alkyl-N-phenylthiocarbamate of the formula (1) is O-ethyl-N-phenylthiocarbamate.

4. A method for repelling insects, ticks and mites, comprising administering, to a desired locus, a repellent effective amount of the composition of claim 1.

* * * * *